(12) United States Patent
Pedain

(10) Patent No.: US 10,261,103 B2
(45) Date of Patent: Apr. 16, 2019

(54) LABORATORY SAMPLE DISTRIBUTION SYSTEM AND LABORATORY AUTOMATION SYSTEM

(71) Applicant: Roche Diagnostics Operations, Inc., Indianapolis, IN (US)

(72) Inventor: Christoph Pedain, Munich (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 295 days.

(21) Appl. No.: 15/405,369

(22) Filed: Jan. 13, 2017

(65) Prior Publication Data

US 2017/0131307 A1 May 11, 2017

Related U.S. Application Data

(63) Continuation of application No. PCT/EP2015/066907, filed on Jul. 23, 2015.

(30) Foreign Application Priority Data

Jul. 23, 2014 (EP) .................................. 14178175

(51) Int. Cl.
*G01N 35/00* (2006.01)
*G01N 35/04* (2006.01)
*G05D 1/02* (2006.01)

(52) U.S. Cl.
CPC ....... *G01N 35/00871* (2013.01); *G01N 35/04* (2013.01); *G05D 1/0297* (2013.01); *G01N 2035/00772* (2013.01); *G01N 2035/00792* (2013.01); *G01N 2035/0489* (2013.01); *G01N 2035/0491* (2013.01); *G01N 2035/0493* (2013.01); *G05D 2201/0206* (2013.01)

(58) Field of Classification Search
CPC .............................. G05D 1/0297; G05D 1/021
See application file for complete search history.

(56) References Cited

U.S. PATENT DOCUMENTS

| | | | | |
|---|---|---|---|---|
| 2006/0184013 | A1* | 8/2006 | Emanuel | G01S 5/16 600/426 |
| 2007/0276558 | A1 | 11/2007 | Kim | |
| 2014/0202829 | A1* | 7/2014 | Eberhardt | G01N 35/04 198/341.01 |

FOREIGN PATENT DOCUMENTS

| | | |
|---|---|---|
| EP | 2500871 A1 | 9/2012 |
| WO | 2012/158541 A1 | 11/2012 |
| WO | 2013/177163 A1 | 11/2013 |

OTHER PUBLICATIONS

International Search Report dated Oct. 14, 2015, in Application No. PCT/EP2015/066907, 4 pages.

* cited by examiner

*Primary Examiner* — Eric S. McCall
*Assistant Examiner* — Timothy P Graves
(74) *Attorney, Agent, or Firm* — Roche Diagnostics Operations, Inc.

(57) ABSTRACT

A laboratory sample distribution system and a laboratory automation system comprising such a laboratory sample distribution system are presented. The laboratory sample distribution system comprises a number of sample container carriers adapted to move autonomously and to communicate with each other and with a central control unit.

20 Claims, 2 Drawing Sheets

LABORATORY SAMPLE DISTRIBUTION SYSTEM AND LABORATORY AUTOMATION SYSTEM

CROSS-REFERENCE TO RELATED APPLICATIONS

This application is a continuation of PCT/EP2015/066907, filed Jul. 23, 2015, which is based on and claims priority to EP 14178175.7, filed Jul. 23, 2014, which is hereby incorporated by reference.

BACKGROUND

The present disclosure relates to a laboratory sample distribution system and to a laboratory automation system comprising such a sample distribution system.

Laboratory sample distribution systems are typically used in order to distribute or transport samples, for example blood or other medical samples, between laboratory stations. The laboratory stations can be used in order to analyze the samples or in order to perform other tasks like capping or identification. An arrangement of laboratory stations with a laboratory sample distribution system can be called a laboratory automation system.

Laboratory sample distribution systems are typically used in order to significantly increase a throughput through laboratory automation systems and to significantly decrease a time needed to do typical analyzing tasks. Known laboratory sample distribution systems may, for example, comprise magnetically driven sample container carriers that are adapted to carry sample containers over a transport plane.

There is a need for an alternative laboratory sample distribution system and to provide a laboratory automation system comprising such a laboratory sample distribution system.

SUMMARY

According to the present disclosure, a laboratory sample distribution system is presented. The laboratory sample distribution system can comprise a plurality of transport planes arranged adjacent to each other. Each transport plane can be divided into a plurality of fields. Each field can have a unique code on the respective transport plane. The transport planes with respect to each other can have partially or completely overlapping codes. The laboratory sample distribution system can further comprise at least one sample container carrier movable on the transport plane and adapted to carry one or more sample containers. The sample container carrier can comprise a code recognition device adapted to recognize the code of the field on which the sample container carrier is currently located, a driver adapted to propel the sample container carrier on the transport plane and/or to set a direction in which the sample container carrier is moving, a controller adapted to control the driver, and a carrier wireless communication device communicatively connected to the controller. The laboratory sample distribution system can further comprise a control unit, a central wireless communicator communicatively connected to the control unit and adapted to communicate with the carrier wireless communicator of the sample container carrier, and a radio frequency position determining device adapted to determine the transport plane on which the sample container carrier is currently located based on a field strength of a signal transmitted between the central wireless communicator and the carrier wireless communicator. The control unit can be adapted to send a transport task to the sample container carrier using the central wireless communicator. The controller can be adapted to control the driver such that the sample container carrier can move according to the received transport task.

Accordingly, it is a feature of the embodiments of the present disclosure to provide an alternative laboratory sample distribution system and to provide a laboratory automation system comprising such a laboratory sample distribution system. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
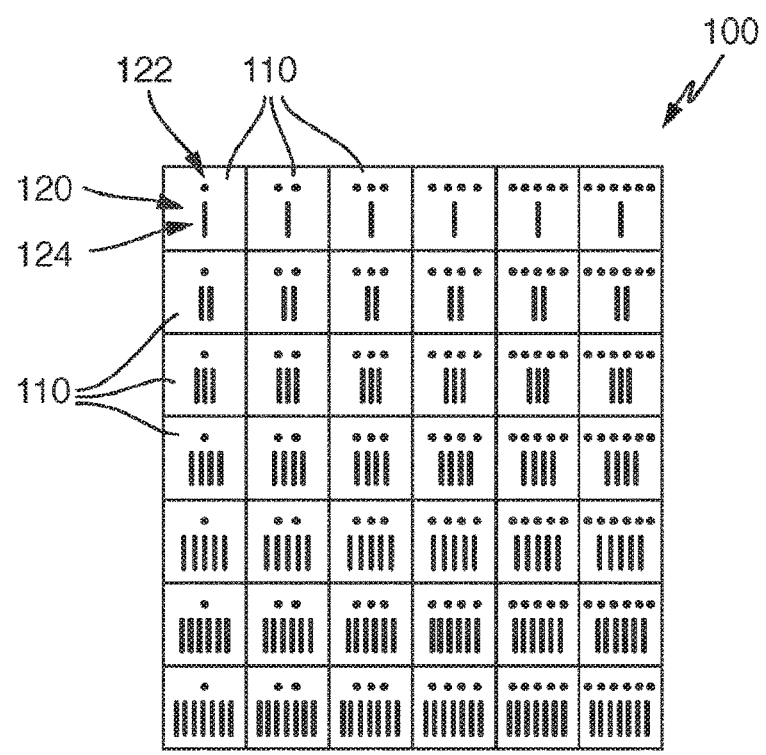
FIG. 1 illustrates schematically a transport plane according to an embodiment of the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A laboratory sample distribution system can comprise at least one transport plane divided into a plurality of fields. Each field can have a unique code on the transport plane. The laboratory sample distribution system can further comprise a number (1 to 1000) of sample container carriers movable on the transport plane and adapted to carry, or contain, one or more sample containers. The sample container carrier can comprise a code recognition device adapted to recognize, or read, the code of the field on which the sample container carrier is currently located. The sample container carrier can further comprise a driver adapted to propel the sample container carrier on the transport plane and/or to set a direction in which the sample container carrier is moving. The sample container carrier can further comprises a controller, e.g. in form of a microprocessor, adapted to control the driver. The sample container carrier can further comprise a carrier wireless communicator communicatively connected to the controller.

The laboratory sample distribution system can further comprise a control unit and a central wireless communicator adapted to wirelessly communicate with the carrier wireless communicator of the sample container carrier. The control unit can be adapted to send transport tasks to the sample container carriers using the central wireless communicator. The controllers can be each adapted to control the respective drivers such that the sample container carriers move according to the respective received transport tasks.

By the laboratory sample distribution system, it can be possible to easily distribute or transport samples and/or sample containers between laboratory stations using self-propelled sample container carriers. This can allow for a high degree of flexibility when designing and operating the laboratory sample distribution system.

The transport plane can typically be a substantially flat plane, for example a floor mat, adapted to carry the sample container carriers. The structuring of the transport plane into fields each having a unique code can allow for an easy and reliable recognition of a respective position of a sample container carrier. A sample container carrier may, for example, have the form of a shuttle or can be denoted as a shuttle. The shuttle can typically be used in order to distribute sample containers, for example between laboratory stations.

In order to carry one or more sample containers, the sample container carry may, for example, be equipped with a sample container holder. Sample containers can typically be implemented as tubes made of transparent material and having an opening at the upper side. Such tubes can, for example, be carried using a cone-shaped holder and/or laterally abutting springs.

The driver can, for example, be implemented having a plurality of wheels or chains that can be adapted to move the sample container carrier on the transport plane. Velocity can typically be controlled by adjusting an angular velocity of the wheels or chains. The direction in which the sample container carrier is moving can, for example, be controlled by tilting one or more wheels or chains or by applying different angular velocities to wheels or chains. For example, a driver can comprise three or four wheels.

The controller and the control unit may each be implemented as a microcontroller, a microprocessor, another electric or electronic device, an application specific integrated circuit (ASIC) or a field programmable gate array (FPGA). The controller and/or the control unit may comprise a processor and memory. The memory can comprise code that, when executed by the processor, can control the behavior of the processor in a certain way.

The central wireless communicator and/or the carrier wireless communicator can, for example, be implemented according to a wireless LAN, Bluetooth, ZigBee, or other known wireless communication standard. They may also be implemented using any other methods for sending and receiving electromagnetic radiation or by using sliding contacts.

The carrier wireless communicator may typically receive commands, for example, from the control unit, and forward them to the controller. The carrier wireless communicator may also send information from the controller to the control unit or to other sample container carriers.

A transport task may, for example, comprise information about an intended end point of movement or a destination for the sample container carrier, i.e. a place where the sample container carrier should move to, or it may, for example, contain a path of movement or low-level driving commands that can instantaneously be performed by the driver.

In a typical embodiment, the controller of a respective sample container carrier can be adapted to control the driver of the respective sample container carrier such that the sample container carrier can move according to a received transport task. Thus, typically each sample container carrier can be adapted to control its movement with a high or low degree of autonomy.

According to an embodiment, the code can be optically recognizable. By this embodiment, the code recognition device may comprise an optical detector. Thus, the optical detector can recognize the optically recognizable code and may thus provide information in order to determine the position of the sample container carrier on the transport plane. The optical detector can, for example, be implemented as a camera, a phototransistor, a photo element or another entity able to recognize the code.

According to an embodiment, the fields can be arranged in a two-dimensional array on the transport plane. A respective code can comprise a first part and a second part. The first part of the code can be indicative of the field's location in a first dimension of the array and the second part of the code can be indicative of the field's location in a second dimension of the array. With this embodiment, each field of the transport plane can have a unique code, in which it can be easily derivable where the sample container carrier is located. For example, the first part may comprise a number of points. The number of points can increase with the distance of the respective field from an edge of the transport plane. The second part may, for example, comprise a number of lines. The number of lines can increase with the distance of the respective field from another edge of the transport plane. This can lead to a unique and easily recognizable code for each field.

According to an embodiment, a plurality of transport planes can be arranged adjacent to each other. A radio frequency position determining device can be adapted to determine the transport plane on which the sample container carrier is currently located based on field strength of a signal transmitted between the central wireless communicator and the carrier wireless communicator. This can allow for an easy scaling of the laboratory sample distribution system. For example, a plurality of transport planes may be arranged according to the needed total size of the laboratory sample distribution system. The radio frequency position determining device may be implemented according to a wireless communication standard or a wireless position determining standard, for example using triangulation and/or field strength measurements. It may, as an example, be implemented using Bluetooth technology. The radio frequency position determining device can be typically configured such that it can be able to securely identify the transport plane on which the sample container carrier is actually located. It may not be necessary that radio frequency position determining device is adapted to determine on which field of the transport plane the sample container carrier is actually located. If the sample container carrier is located adjacent to an outer edge of a transport plane, it may not be possible to identify the transport plane using the radio frequency position determining device alone. However, in this case, it can be determined using the codes and the code recognition device at which outer edge of a transport plane the sample container carrier is located, so that it can also be derived on which transport plane it is located.

Several, or all, of the plurality of transport planes may be similar, or identical, to each other, i.e., the transport planes with respect to each other may have partially or completely overlapping codes. This may imply that one or more codes are not unique within the laboratory sample distribution system. By the radio frequency position determining device, it can be possible to determine the transport plane on which the sample container carrier is currently located and thus to resolve problems with non-unique codes occurring on different transport planes.

According to an embodiment, the control unit can comprise a central position surveillance device adapted to check and/or ensure proper execution of transport tasks, and/or to inform connected systems about approaching sample container carriers, and/or to avoid collisions between the sample container carriers. Such central position surveillance device can, for example, comprise a camera adapted to identify respective positions of the sample container carriers. The central position surveillance device can also receive signals from the sample container carriers indicative of respective positions that can be determined using the code recognition device and/or the radio frequency position determining device. The central position surveillance device can, for example, check if a collision is about to occur between at least two sample container carriers and can send signals to one or more of such sample container carriers in order to change their direction, or velocity, in order to stop at least one of the sample container carriers.

According to an embodiment, the carrier wireless communicator can be adapted to communicate directly and/or via a number of central communication hubs with carrier wireless communicators of other sample container carriers. This can allow for the embodiment of tasks like collision avoidance or self-organization of the sample container carriers. Central communication hubs can, for example, be positioned besides, above or in the transport plane.

According to an embodiment, the controller can be adapted to send a position, direction and/or velocity of the sample container carrier to other sample container carriers and/or to the control unit, and/or to receive a position, direction and/or velocity of another sample container carrier. This may be used for example in order to avoid collisions or in order to implement self-organizing capabilities that can be used, for example, according to embodiments discussed further below. Typically, the controller of a respective sample container carrier can send or receive information from that sample container carrier or intended for that sample container carrier.

According to an embodiment, the controller of the respective sample container carrier can be adapted to resolve a received transport task and to calculate a transport path for the sample container carrier based on the transport task. With this embodiment, it can be possible for the control unit to simply send transport tasks including information like intended destination to the sample container carrier. The sample container carrier can move autonomously to that destination. This can allow for a certain degree of self-organization of the sample container carriers on the transport plane.

According to an embodiment, the controller of the respective sample container carrier can be further configured to calculate the transport path taking into account one or more positions, directions and/or velocities of other sample container carriers. This can be useful in order to calculate a fastest path and to avoid collisions with other sample container carriers.

According to an embodiment, the controller of the respective sample container carrier can be configured to calculate an intended velocity of the sample container carrier along the transport path. This can, for example, be used in order to take into account current or estimated positions of other sample container carriers and to calculate the fastest transport path.

According to an embodiment, the controller of the respective sample container carrier can be configured to control the driver such that the sample container carrier moves along the transport path and/or with the intended velocity. This allows for self-control of the driver of the sample container carrier by the controller.

According to an embodiment, the controller of the respective sample container carrier can be configured to send a request for supplemental material to another sample container carrier and/or to the control unit. For example, supplemental material may be reagents, or other chemical substances, needed by a specific analytical station or by another entity coupled to the laboratory sample distribution system. The request may comprise information regarding one or more of a type of supplemental material, a destination where the supplemental material is needed, a time when the supplemental material is needed, and an amount of supplemental material.

It can be noted that requests for supplemental material may be implemented on a variety of different levels. For example, the controller may specifically direct a certain sample container carrier to bring a certain type of supplemental material to a certain destination, for example an analytical station. The request may also be implemented such that it may only contain the information about what kind of supplemental material is needed in which amount at which destination so that other sample container carriers can estimate on their own if they are eligible for delivering such supplemental material.

With this embodiment, it can be possible that a sample container carrier itself can request supplemental material required to analyze a sample it is currently carrying. This can significantly reduce central surveillance requirements.

According to an embodiment, the controller of the respective sample container carrier can be configured to receive a request for supplemental material from another sample container carrier and/or from the control unit. The request may comprise information regarding one or more of a type of supplemental material, a destination where the supplemental material is needed, a time when the supplemental material is needed, and an amount of supplemental material.

The controller may be configured to check if the sample container carrier is loaded with supplemental material fulfilling the request and, in response to determining that the sample container carrier is loaded with supplemental material fulfilling the request, to deliver the supplemental material according to the request and/or to send a response to the control unit and/or to the other sample container carrier indicating that the request can be fulfilled. This can allow for self-determination of the sample container carrier if it is eligible to fulfill such a request based upon its determination that it is loaded with the correct supplemental material.

The controller may also be configured to check if the sample container carrier is empty and, in response to determining that the sample container carrier is empty, to catch or load supplemental material fulfilling the request and to deliver the supplemental material according to the request and/or to send a response to the control unit and/or to the other sample container carrier indicating that the request can be fulfilled. This can allow for self-determination of the sample container carrier if it is eligible to fulfill the request based on its determination that it is empty and is able to catch or load the supplemental material and to deliver it to the intended destination.

The above described embodiments may be used in order to implement a certain degree of self-organization of the sample container carriers on the transport plane. By informing a requesting sample container carrier or the control unit, a requesting entity gets a feedback that its job will be fulfilled by a certain sample container carrier.

According to an embodiment, delivering the supplemental material can comprise calculating, by the controller of the respective sample container carrier, a transport path to a destination and controlling the driver of the respective sample container carrier such that the sample container carrier can move according to the calculated transport path. According to a further embodiment, catching or loading the supplemental material can comprise calculating, by the controller of the respective sample container carrier, a transport path to a supply station where the supplemental material is available and controlling the driver of the respective sample container carrier such that the sample container carrier can move according to the calculated transport path. These embodiments can allow for a certain degree of self-organization of the sample container carriers when fulfilling requests for supplemental material.

The control unit may be adapted to update programming, software, firmware or other behavior determining methods of the sample container carriers by wireless communication. This can allow, for example, adaption of algorithms used by the controllers of the sample container carriers according to current workload, tasks or system status.

A laboratory automation system can comprise a number of laboratory stations such as, for example, pre-analytical, analytical and/or post-analytical stations, and a laboratory sample distribution system adapted to distribute sample containers between the laboratory stations. The laboratory stations may be arranged adjacent to the laboratory sample distribution system.

Pre-analytical stations may be adapted to perform any kind of pre-processing of the samples, of the sample containers and/or of the sample container carriers.

Analytical stations may be adapted to use the sample or part of the sample and a reagent to generate a measuring signal, the measuring signal indicating if and in which concentration, if any, an analyte exists.

Post-analytical stations may be adapted to perform any kind of post-processing of the samples, the sample containers and/or the sample container carriers.

The pre-analytical, analytical and/or post-analytical stations may comprise at least one of a decapping station, a recapping station, an aliquot station, a centrifugation station, an archiving station, a pipetting station, a sorting station, a tube type identification station, and a sample quality determining station.

According to an embodiment, at least one of the number of laboratory stations can be configured to send a request for supplemental material to the sample container carrier and/or to the control unit. The request may comprise information regarding one or more of a type of supplemental material, a destination where the supplemental material is needed, a time when the supplemental material is needed, and an amount of supplemental material.

The laboratory system may further comprise a supplemental material supply station adapted to load the sample container carrier with the supplemental material. By such an embodiment, the sample container carriers can provide for a delivery of supplemental material with a certain degree of self-organization. Efforts to centrally control and administer the laboratory automation system or the laboratory sample distribution system may thus be minimized.

The supplemental material supply station may be adapted to load typical supplemental materials needed by the analytical stations. For example, it can be adapted to provide for sample containers already loaded with such materials like chemical reagents such that the sample containers can readily be loaded on the sample container carriers. A supplemental material supply station can also be adapted such that it is able to fill empty sample containers with the respective supplemental material.

According to an embodiment, the at least one of the number of laboratory stations can be configured to send a status information to the control unit and/or to the sample container carrier. The status information may comprise one or more of a current queue of unprocessed samples, a current or future need for supplemental material, an estimated processing time, and an index relating to current and/or future workload.

This information may be used in organizing or self-organizing the sample container carriers on the transport plane. The current queue of unprocessed samples or an estimated processing time gives information about the current capability of the laboratory station to timely perform a task, like analyzing a sample. A current or future need for supplemental material may be used in order to plan transport tasks that should be performed by sample container carriers. The index relating to current and/or future workload may be used in order to plan if it is realistic to timely process a sample at the laboratory station.

Referring initially to FIG. 1, FIG. 1 shows a transport plane 100 according to an embodiment. The transport plane 100 can comprise a number (42) of fields 110, which can be equally distributed over the transport plane 100 and can be arranged in six rows and seven lines.

Each field 110 can comprise a code 120. Each code 120 can comprise a first element 122 and a second element 124. The first element 122 can comprise a number of dots. The number of dots can correspond to the number of the column, taken from the left edge of the transport plane 100. The second element 124 can comprise a number of lines. The number of lines can correspond to the number of the row taken from an upper edge of the transport plane 100. The second element 124 can be arranged below the respective first element 122.

The code 120 can be unique for each field 110. This can allow an entity moving on the transport plane 100, for example a sample container carrier 200 as described below with reference to FIG. 2, to determine its position on the transport plane 100 by reading the code 120 and by analyzing the number of dots in the first element 122 and the number of lines in the second element 124.

Figure 2:
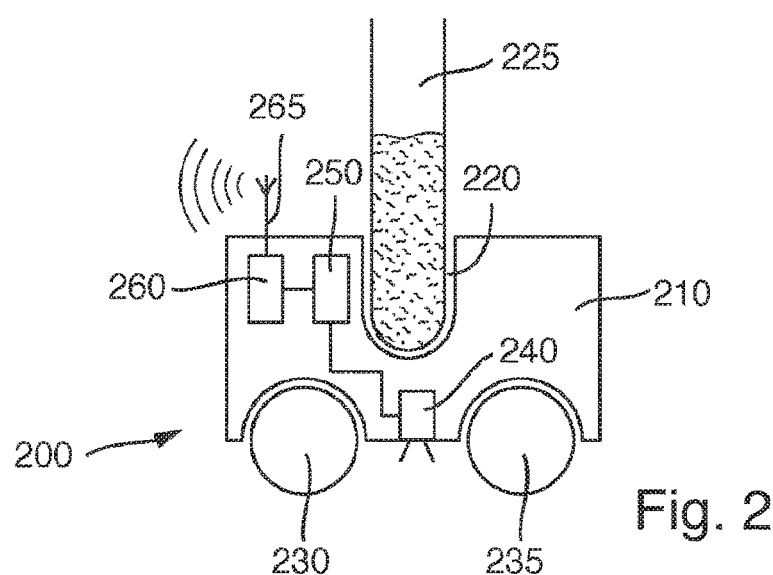
FIG. 2 illustrates schematically a sample container carrier carrying a sample container according to an embodiment of the present disclosure.

FIG. 2 shows a sample container carrier 200. The sample container carrier 200 can be adapted to move on a transport plane 100 as shown in FIG. 1. The sample container carrier 200 can comprise a main body 210, in which a holder 220 can be formed. The holder 220 can be adapted to carry a sample container 225. The sample container 225 can be a tube having an open upper side and can be filled with a sample.

The sample container carrier 200 can comprise a driver having a first wheel 230 and a second wheel 235. It can be noted that the driver can comprise four wheels. Two of the wheels are not depicted in FIG. 2 due to the perspective.

The wheels 230, 235 can be driven by motors that are not shown in FIG. 2. Two of the four wheels 230, 235 may be tilted in order to set a direction in which the sample container carrier 200 is moving. The wheels 230, 235 can thus allow for a controlled movement of the sample container carrier 200 over the transport plane 100.

The sample container carrier 200 can further comprise a code recognition device 240 implemented as a camera. The camera 240 can be situated at the bottom of the main body 210 and can look to the plane on which the sample container carrier 200 stands or is moving. Thus, the camera 240 can be adapted to see the code 120 when the sample container carrier 200 is moving over the transport plane 100 of FIG. 1.

The sample container carrier 200 can further comprise a controller 250 which can be, inter alia, adapted to control the motors driving the wheels 230, 235 and to control a tilting angle of the tiltable wheels.

The sample container carrier 200 can further comprise a carrier wireless communicator 260 implemented as a wireless module having an antenna 265. The carrier wireless communicator 260 can be connected with the controller 250 in order to provide a communications capability to the controller 250. By the carrier wireless communicator 260, the controller 250 may send and receive signals to and from other sample container carriers 200 or a central control unit.

As shown and described up to now, the sample container carrier 200 can transport the sample container 225 over the transport plane 100 of FIG. 1 without any need for external drivers. This can mean that the sample container carrier 200 can drive on its own. The typical operation of the sample container carrier 200 in a laboratory sample distribution system is discussed further below with reference to FIG. 3.

Figure 3:
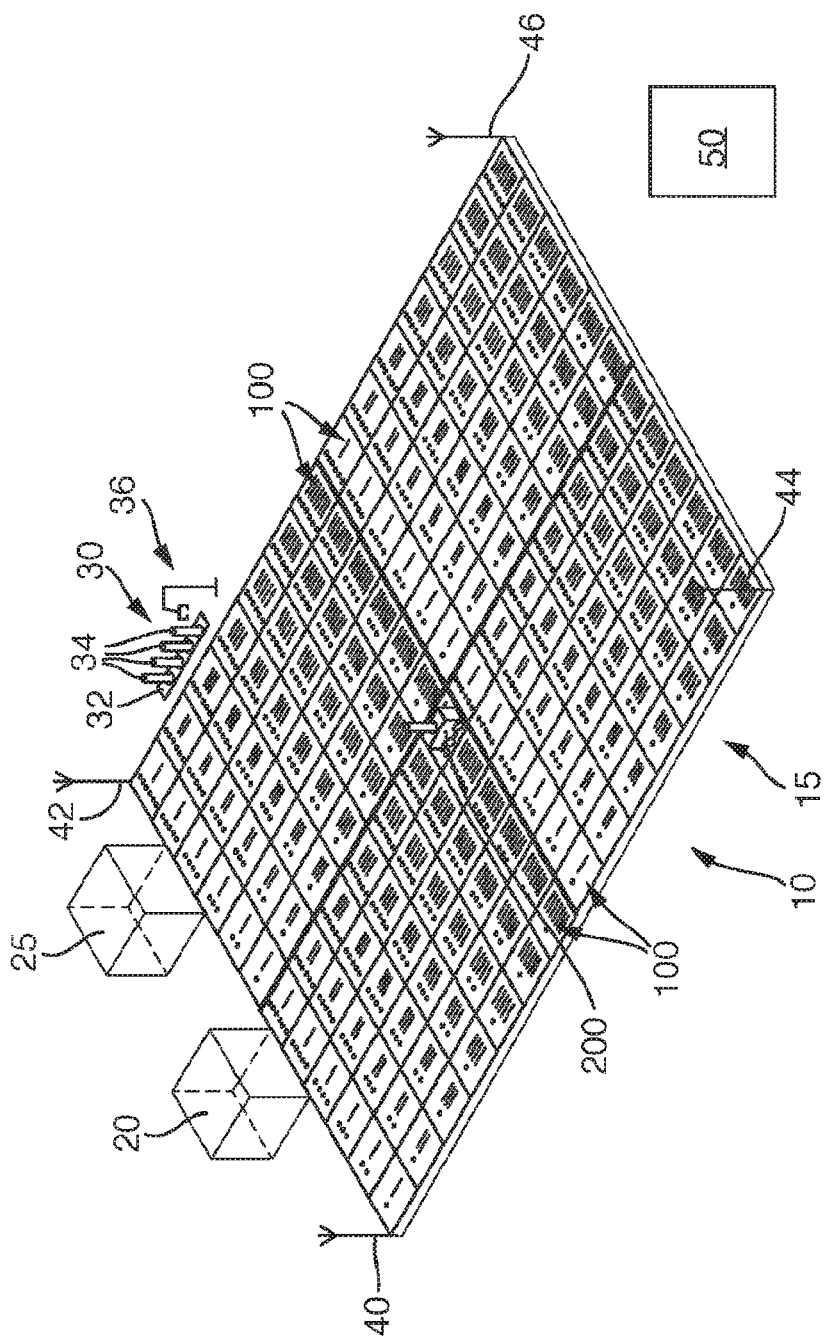
FIG. 3 illustrates schematically a laboratory automation system comprising a laboratory sample distribution system according to an embodiment of the present disclosure.

FIG. 3 shows a laboratory automation system 10 comprising a laboratory sample distribution system 15. The laboratory sample distribution system 15 can comprise four transport planes 100 as shown in FIG. 1. The transport planes 100 can be positioned adjacent to each other such that the resulting area covered by the four transport planes 100 can have a substantially rectangular shape.

The laboratory sample distribution system 15 can further comprise a number of sample container carriers 200 according to the embodiment shown in FIG. 2. In order to simplify FIG. 3, only one such sample container carrier 200 is shown in FIG. 3. It can be noted that typically a plurality of sample container carriers 200 can be placed on the transport planes 100.

The laboratory sample distribution system 15 can further comprise four antennas 40, 42, 44, 46 that can be part of a central wireless communicator. The central wireless communicator can comprise further conventional circuits, not explicitly depicted, adapted for wireless communication. The central wireless communicator can be adapted to communicate with each of the sample container carriers 200. As a counterpart, the carrier wireless communicator 260 comprising the antenna 265, as described above with reference to FIG. 2, can be used on the side of the respective sample container carrier 200.

The laboratory sample distribution system 15 can further comprise a control unit 50 adapted to communicate with the sample container carriers 200 using the central wireless communicator.

The laboratory automation system 10 can further comprise a first laboratory station 20 and a second laboratory station 25. The laboratory stations 20, 25 can be adapted to perform certain analytical tasks with samples contained in sample containers 225 and can thus also be denoted as analytical stations. The sample container carriers 200 can be used to transport sample containers 225 to and from the analytical stations 20, 25. The control unit 50 can be configured to send suitable drive commands to the sample container carriers 200 when they contain a sample container 225 with a sample. The drive commands can comprise a destination for the respective sample. The control entity 225 of the sample container carrier 200 can receive a respective drive command and autonomously calculates a suitable path to this destination. When calculating this path, information about the current position of the sample container carrier 200 and information about current positions, velocities and directions of other sample container carriers 200 can be taken into account. This can allow for a highly autonomous movement of the sample container carrier 200.

In order to determine the position of the sample container carrier 200, the camera 240 can read the code 120 of the transport plane 100 on which the sample container 200 is currently positioned. However, this information may not yet be sufficient in order to determine the absolute position of the sample container carrier 200, because each code 120 can occur four times in the laboratory sample distribution system 15. In order to determine the position exactly, the carrier wireless communicator or wireless module 260 can be adapted to perform triangulation measurements using the antennas 40, 42, 44, 46 of the laboratory sample distribution system 15. Using this triangulation, it can be possible to approximately determine the position of the sample container carrier 200, however with less accuracy than using the code 120. Taking both sets of information together, the position can be calculated exactly. In detail, the information from the triangulation can be used to determine on which of the four transport planes 100 the sample container carrier 200 is located, and the information from the code 120 can be used to determine on which field 110 of this transport plane 100 the sample container carrier 200 is located.

The position, that is determined as described, can also be used by the controller 250 in order to ensure that the sample container carrier 200 is moving along the calculated path and with an intended velocity.

The analytical stations 20, 25 may need some supplemental materials like chemical reagents in order to analyze the samples. Therefore, the laboratory automation system 10 can further comprise a supplemental material supply station 30 adapted to load sample containers with such supplemental materials on sample container carriers 200. In detail, the supplemental material supply station 30 can comprise a holding unit 32 adapted to hold a plurality of sample containers 34. Only four sample containers 34 are shown in FIG. 3 for the sake of simplicity. The supplemental material supply station 30 can further comprise a handler 36 adapted to take out a sample container 34 from the holder 32 and to load the respective sample container 34 on the sample container carrier 200.

If one of the analytical stations 20, 25 needs a certain supplemental material, it can report this need to the control unit 50. The control unit 50 can send a respective message containing the information about the needed supplemental material and the destination, i.e., the demanding analytical station 20, 25, over the antennas 40, 42, 44, 46 to the sample container carriers 200. If a controller 250 of a sample container carrier 200 determines that the sample container carrier 200 is currently empty, i.e., it does not contain a sample container 225, it can send a response to the control unit 50. The response can indicate that the sample container carrier 200 is able to supply the needed supplemental material to the demanding analytical station 20, 25. Then, the controller 250 can calculate a path to the supplemental material supply station 30 and control, or drive, the wheels 230, 235 such that the sample container carrier 200 moves along this path. At the supplemental material supply station 30, the sample container carrier 200 can be loaded with a sample container 34 containing the requested supplemental material. Then, the controller 250 can calculate a path to the demanding analytical station 20, 25 and control the wheels 230, 235 such that the sample container carrier 200 moves along this path. At the demanding analytical station 20, 25, the sample container 34 can be unloaded by the analytical station 20, 25 and the supplemental material can be used by the demanding analytical station 20, 25. This can allow for a supply of the analytical station 20, 25 with supplemental material by the sample container carriers 200 moving on the transport planes 100 and can thus omit the need for further supply logistics.

The controller 250 of each sample container carrier 200 can be further adapted to periodically send position, velocity and direction information over the respective carrier wireless communicator 260. This information can be received by other sample container carriers 200 and by the antennas 40, 42, 44, 46 for forwarding to the control unit 50. This can allow other sample container carriers 200 to take this information into account in order to avoid collisions. Furthermore, the control unit 50 can have an overview over the position of each of the sample container carriers 200 and can also run an independent collision avoidance system.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A laboratory sample distribution system, the laboratory sample distribution system comprising:
   a plurality of transport planes arranged adjacent to each other, wherein each transport plane is divided into a plurality of fields, wherein each field has a unique code on the respective transport plane, wherein the transport planes with respect to each other have partially or completely overlapping codes;
   at least one sample container carrier movable on the transport plane and adapted to carry one or more sample containers, the sample container carrier comprising,
      a code recognition device adapted to recognize the code of the field on which the sample container carrier is currently located,
      a driver adapted to propel the sample container carrier on the transport plane and/or to set a direction in which the sample container carrier is moving,
      a controller adapted to control the driver, and
      a carrier wireless communication device communicatively connected to the controller;
   a control unit;
   a central wireless communicator communicatively connected to the control unit and adapted to communicate with the carrier wireless communicator of the sample container carrier; and
   a radio frequency position determining device adapted to determine the transport plane on which the sample container carrier is currently located based on a field strength of a signal transmitted between the central wireless communicator and the carrier wireless communicator, wherein the control unit is adapted to send a transport task to the sample container carrier using the central wireless communicator, and wherein the controller is adapted to control the driver such that the sample container carrier moves according to the received transport task.

2. The laboratory sample distribution system according to claim 1, wherein the code is optically recognizable.

3. The laboratory sample distribution system according to claim 1, wherein the code recognition device comprises an optical detector.

4. The laboratory sample distribution system according to claim 1, wherein the fields are arranged in a two-dimensional array on the transport plane and a respective code comprises a first part and a second part, wherein the first part is indicative of the field's location in a first dimension of the array and wherein the second part is indicative of the field's location in a second dimension of the array.

5. The laboratory sample distribution system according to claim 1, wherein the carrier wireless communicator is adapted to communicate directly and/or via a number of central communication hubs with carrier wireless communicators of other sample container carriers.

6. The laboratory sample distribution system according to claim 1, wherein the controller is adapted to send a position, direction and/or velocity of the sample container carrier to other sample container carriers.

7. The laboratory sample distribution system according to claim 1, wherein the controller is adapted to receive a position, direction and/or velocity of another sample container carrier.

8. The laboratory sample distribution system according to claim 1, wherein the controller is adapted to calculate a transport path for the sample container carrier based on the transport task.

9. The laboratory sample distribution system according to claim 8, wherein the controller is configured to control the driver such that the sample container carrier moves along the transport path.

10. The laboratory sample distribution system according to claim 1, wherein the controller is configured to send a request for supplemental material to another sample container carrier and/or to the control unit.

11. The laboratory sample distribution system according to claim 10, wherein the request comprising information regarding one or more of a type of supplemental material, a destination where the supplemental material is needed, a time when the supplemental material is needed, and an amount of supplemental material.

12. The laboratory sample distribution system according to claim 1, wherein the controller is configured to receive a request for supplemental material from another sample container carrier and/or from the control unit.

13. The laboratory sample distribution system according to claim 12, wherein the request comprising information regarding one or more of a type of supplemental material, a destination where the supplemental material is needed, a time when the supplemental material is needed, and an amount of supplemental material.

14. The laboratory sample distribution system according to claim 13, wherein the controller is configured to check if the sample container carrier is loaded with supplemental material fulfilling the request, and in response to determining that the sample container carrier is loaded with supplemental material fulfilling the request delivering the supplemental material according to the request, and/or sending a response to the control unit and/or to the other sample container carrier indicating that the request can be fulfilled.

15. The laboratory sample distribution system according to claim 14, wherein delivering the supplemental material comprises calculating, by the controller, a transport path to a destination and controlling the driver such that the sample container carrier moves according to the calculated transport path.

16. The laboratory sample distribution system according to claim 13, wherein the controller is configured to check if the sample container carrier is empty, and in response to determining that the sample container carrier is empty, to catch supplemental material fulfilling the request and to deliver the supplemental material according to the request, and/or to send a response to the control unit and/or to the other sample container carrier indicating that the request can be fulfilled.

17. The laboratory sample distribution system according to claim 16, wherein catching the supplemental material comprises calculating, by the controller, a transport path to a supply station where the supplemental material is available and controlling the driver such that the sample container carrier moves according to the calculated transport path.

18. A laboratory automation system, the laboratory automation system comprising:
   a number of laboratory stations, preferably pre-analytical, analytical and/or post-analytical stations; and
   a laboratory sample distribution system according to claim 1 adapted to distribute sample containers between the laboratory stations.

19. The laboratory automation system according to claim 18, wherein at least one of the number of laboratory stations is configured to send a request for supplemental material to the sample container carrier and/or to the control unit, the request comprising information regarding one or more of a type of supplemental material, a destination where the supplemental material is needed, a time when the supplemental material is needed, and an amount of supplemental material, wherein the laboratory automation system comprises a supplemental material supply station adapted to load the sample container carrier with the supplemental material.

20. The laboratory automation system according to claim 18, wherein at least one of the number of laboratory stations is configured to send a status information to the control unit and/or to the sample container carrier, wherein the status information comprises one or more of a current queue of unprocessed samples, a current or future need for supplemental material, an estimated processing time, and an index relating to current and/or future workload.

* * * * *